(12) United States Patent
Kopperschmidt

(10) Patent No.: US 8,043,076 B2
(45) Date of Patent: Oct. 25, 2011

(54) METHOD AND DEVICE FOR OPERATING AN ELECTRIC PERISTALTIC HOSE PUMP

(75) Inventor: Pascal Kopperschmidt, Dittelbrunn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 661 days.

(21) Appl. No.: 12/282,544

(22) PCT Filed: Mar. 1, 2007

(86) PCT No.: PCT/EP2007/001754
§ 371 (c)(1),
(2), (4) Date: Sep. 11, 2008

(87) PCT Pub. No.: WO2007/104435
PCT Pub. Date: Sep. 20, 2007

(65) Prior Publication Data
US 2009/0053083 A1    Feb. 26, 2009

(30) Foreign Application Priority Data
Mar. 11, 2006  (DE) .......................... 10 2006 011 346

(51) Int. Cl.
*F04B 43/12*    (2006.01)
(52) U.S. Cl. .................. 417/476; 417/477.1; 417/477.2; 417/477.3; 417/477.4
(58) Field of Classification Search ........ 417/44.1–44.2, 417/53, 476, 477.1–477.4, 477.8, 477.7, 417/477.11; 604/20
See application file for complete search history.

(56) References Cited

U.S. PATENT DOCUMENTS
5,629,871 A    5/1997    Love et al.

FOREIGN PATENT DOCUMENTS
| EP | 1 156 214 | 11/2001 |
|---|---|---|
| WO | WO 93/12827 | 7/1993 |
| WO | WO 94/20157 | 9/1994 |
| WO | WO 03/072942 | 9/2003 |

OTHER PUBLICATIONS

International Preliminary Report on Patentability for PCT/EP2007/001754, mailed on Oct. 14, 2008.

*Primary Examiner* — Karabi Guharay
*Assistant Examiner* — Elmito Breval
(74) *Attorney, Agent, or Firm* — Kenyon & Kenyon LLP

(57) ABSTRACT

The invention relates to a method and to a device for operating an electric peristaltic hose pump, in particular a hose pump for transporting fluids in medical-technical devices, in particular extracorporeal blood treatment devices. In order to monitor the regular operation of a hose pump, the power consumption of the pump or a physical variable in correlation with the power consumption, in particular the pump flow, is monitored. The pump flow includes a periodically non-altering direct component which is superimposed on a periodically altering alternating component. In order to monitor the regular operation of the hose pump, the alternating component of the power consumption in relation to the direct component of the power consumption is monitored as whether it increases and/or decreases during blood treatment.

16 Claims, 3 Drawing Sheets

1. Complete occlusion

Power consumption of roller pump time

2. Start of vanishing occlusion

Power consumption of roller pump time

3. Vanishing occlusion

Power consumption of roller pump time

METHOD AND DEVICE FOR OPERATING AN ELECTRIC PERISTALTIC HOSE PUMP

FIELD OF THE INVENTION

The present invention relates to a method and a device for the operation of an electric peristaltic hose pump for conveying a fluid in a hose line. The invention also relates to a method for the operation of an electric peristaltic hose pump of an extracorporeal blood treatment apparatus as well as an extracorporeal blood treatment apparatus with a device for the operation of a peristaltic hose pump.

BACKGROUND

In the case of extracorporeal blood treatment, for example, hemodialysis, the blood to be treated flows in an extracorporeal blood circuit through the blood chamber of a dialyzer divided by a semipermeable membrane into the blood chamber and a dialyzing fluid chamber, whilst in the case of a dialyzing fluid system dialyzing fluid flows through the dialyzing fluid chamber. The extracorporeal blood circuit has an arterial hose line which leads to the blood chamber, and a venous hose line which leads away from the blood chamber. The known hemodialysis apparatuses have a blood pump which is generally arranged upstream of the blood chamber of the dialyzer in order to ensure an adequate flow of blood in the extracorporeal blood circuit.

Great technical demands are made on the blood pump. Only certain types of pump therefore come into consideration. Hose pumps that convey the patient's blood through the arterial and venous hose line have been tried and tested in practice.

According to their mode of operation, hose pumps are also referred to as peristaltic pumps, The pump action is based on the fact that at least one occlusion moves along the elastic hose line serving as the pumping space and thereby displaces the enclosed fluid in the delivery direction.

With the most common design of hose pumps, the adjustment takes place in such a way that the elastic hose is completely occluded at the moved constriction points. These pumps arc therefore also referred to as occlusive hose pumps. The moving constriction points or occlusions that transport the blood in the pump hose can be generated in various ways from the technical standpoint.

Roller pumps are known, wherein the hose is inserted between a stator, which forms a curved roller path as a counter-bearing, and a rotor mounted rotatably therein and fitted with rollers, so that the rollers roll off on the hose in the delivery direction. The rollers may be spring-mounted on the rotor, so that they exert a pressing force on the hose. Finger pumps are also known, wherein the constriction points or occlusions are produced by a series of mobile stamps (fingers) arranged along the hose.

An overview of the various designs of roller and finger pumps is given in Dialysetechnik, 4$^{th}$ edition, Gesellschaft für angewandte Medizintechnik m.b.H. & Co. K G, Friedrichsdorf, 1988.

Electric peristaltic hose pumps are used in the known blood treatment apparatuses not only for conveying the blood, but also for conveying other fluids. Great demands are made on the proper operation of such hose pumps when they are used in medical-technical apparatuses, in particular in blood treatment apparatuses.

During the operation of roller pumps, the problem arises that a complete occlusion of the hose line is no longer produced when there is an increase in the flow resistance. On the contrary, the rollers begin to rise from the hose line. In this case, proper operation of the roller pump is no longer ensured.

U.S. Pat. No. 5,629,871 describes a method and a device for the monitoring of the functional capability of individual subassemblies of a hemodialysis apparatus. These also include hose pumps, whereby the pump current or the voltage is monitored in order to deduce the functional capability of the pump. It is known from U.S. Pat. No. 4,781,525 to use the pump current to determine the delivery rate.

WO 97/45150 describes a method for the determination of the delivery pressure of a pump, wherein the pump current is determined. Since deviations from a linear relationship between the delivery pressure and the pump current can occur under certain circumstances, the use of a calibration curve is proposed.

The problem underlying the invention is to provide a method and a device for the operation of an electric peristaltic hose pump, in particular the hose pump of an extracorporeal blood treatment apparatus, which respectively permit reliable monitoring of the proper operation of the hose pump.

SUMMARY

Underlying example embodiments of the present invention is the knowledge that the power consumption of an electric pump changes with complete or partial occlusion of the hose line by the displacement bodies of the electric peristaltic pump, for example the rollers of a roller pump. An example embodiments of the present invention is based on determining the power consumed by the pump or a physical magnitude correlating with the power, for example, the current consumed by the pump, and determining from the measured physical magnitude a direct component that does not change periodically and an alternating component that changes periodically and is superimposed on the direct component. In order to monitor the proper operation of the hose pump, monitoring is carried out during the blood treatment to establish how the alternating component of the power consumption rises or falls relative to the direct component of the power consumption. It is then concluded that there is an incorrect operation of the hose pump on the basis of the direct component and the alternating component, in particular when there is a characteristic time-related change in the direct component and a time-related change in the alternating component.

In an example embodiment, the power consumption is evaluated by the fact that the time-related change in the direct component and the time-related change in the alternating component in preset time intervals are put into a relationship with one another, whereby an incorrect operation of the hose pump is concluded on the basis of the time-related change in the ascertained relationship between the time-related change in the direct component and alternating component in preset time intervals during the operation of the hose pump.

An example embodiment of the present invention is based in particular on the knowledge that the quotient of the time-related change in the alternating component and the direct component is a characteristic magnitude indicating whether the displacement bodies of the peristaltic pump are occluding the hose line completely or only partially. The quotient may be monitored during the blood treatment, so that in the event that the quotient falls below a specific limiting value, it can be concluded that a complete occlusion is no longer present. Depending on the level of the limiting value, it is possible to establish the degree of the occlusion at which, if fallen below, an incorrect operation of the pump is assumed. A number of limiting values may also be defined which reveal the onset of a disappearing occlusion or which permit the conclusion that there is a malfunction only when the occlusion has already been at least partially removed.

In another example embodiment, the time-related change in the alternating and direct component in preset time intervals, i.e. the derivation of the function or the gradient of the curve, is not determined, but instead the quotient ($A_{AC}/I_{DC}$) of the alternating component (d/dt $A_{AC}$) and the direct component ($I_{DC}$) is calculated in preset time intervals during the operation of the hose pump and compared with the preset limiting value, whereby it is concluded that there is an inadequate occlusion of the hose pump if the quotient falls below the preset limiting value. The quotient of the direct and the alternating component may, however, also be determined, whereby it is concluded that there is an inadequate occlusion of the hose pump if the quotient exceeds the preset limiting value. Other terms can, however, also be used for the evaluation, as long as it is only at the start of the occlusion that they lead to a characteristic change in the calculated magnitude.

The alternating component of the measured physical magnitude which correlates with the power consumption of the pump is dependent on the design of the pump. The frequency of the alternating component is particularly dependent on the number of rollers of the roller pump. Since the frequency of the rotor is known, the alternating component can easily be determined. Known mathematical procedures, including, for example, the Fourier analysis, are suitable for this.

The device according to the invention has a mechanism for determining the direct component and alternating component of the power consumption or the measured physical magnitude that correlates with the power consumption, and a mechanism for ascertaining an incorrect operation of the hose pump. The device according to example embodiments of the invention may form a separate subassembly or be a component part of the known blood treatment apparatuses.

The use of the method according to example embodiments of the invention and the use of the device according to example embodiments of the invention in extracorporeal blood treatment apparatuses, for example hemodialysis apparatuses, has proved to be particularly advantageous for monitoring the proper operation of the blood pump arranged in the extracorporeal blood circuit. The operation of all other hose pumps in medical-technical apparatuses or in general machine constructions can, however, also be monitored with the method according to example embodiments of the present invention and the device according to example embodiments of the present invention.

An example embodiment of the present invention is explained below in greater detail by reference to the drawings.

DETAILED DESCRIPTION

Figure 1:
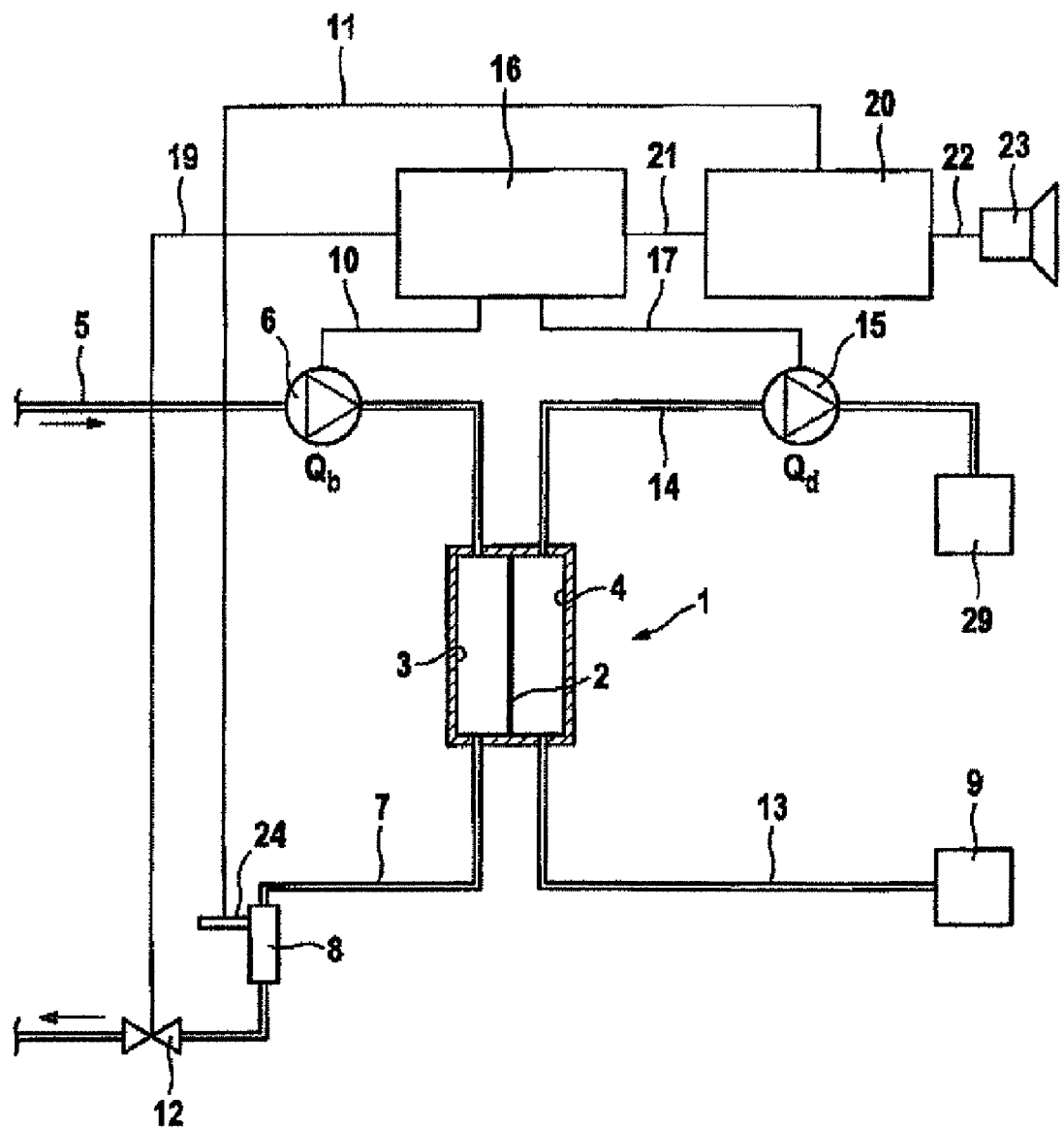
FIG. 1 shows an extracorporeal blood treatment apparatus according to an example embodiment of the present invention, which has a device according to an example embodiment of the invention for the operation of a hose pump of the blood treatment apparatus.

The extracorporeal blood treatment apparatus, in particular a hemodialysis apparatus, has a dialyzer 1, which is divided by a semi-permeable membrane 2 into a blood chamber 3 and a dialyzing fluid chamber 4. An arterial blood line 5, into which a blood pump 6 is incorporated, leads from a patient to an inlet of blood chamber 3, whilst a venous blood line 7 leads from an outlet of the blood chamber via a drip chamber 8 to the patient. An electromagnetically actuated shut-off valve 12 is arranged downstream of drip chamber 8 in venous hose line 7.

The fresh dialyzing fluid is prepared in a dialyzing fluid source 12. From dialyzing fluid source 12, a dialyzing fluid supply line 13 leads to the inlet of dialyzing fluid chamber 4 of dialyzer 1, whilst a dialyzing fluid discharge line 14 leads from an outlet of the dialyzing fluid chamber to a drain 9. A dialyzing fluid pump 15 is incorporated into dialyzing fluid discharge line 14.

Blood pump 6 is an electrically operated peristaltic hose pump, in particular a roller pump, whereby arterial and venous blood lines 5, 7 are flexible hose lines which are inserted into roller pump 6. Venous shut-off valve 12 is an electromagnetically actuatable hose clip.

The dialysis apparatus has a control unit 16 which is connected to blood pump 6 and dialyzing fluid pump 15 via control lines 16, 17. Control unit 16 makes available a specific voltage or a specific current for the operation of blood pump 6 and dialyzing fluid pump 12, so that blood flows in blood lines 5, 7 at a preset blood flow rate $Q_b$ and dialyzing fluid flows in dialyzing fluid lines 13, 14 at a preset dialyzing fluid rate $Q_d$. Moreover, control unit 16 actuates venous shut-off valve 12 via a control line 19.

Apart from control unit 16, the blood treatment apparatus has a computing and analyzing unit 20, which communicates via a data line 21 with control unit 16. Computing and analyzing unit 20 is connected via a further data line 22 to an alarm unit 23, which emits an optical and/or acoustic alarm.

In order to measure the pressure in venous blood line 7, there is arranged at drip chamber 8 a venous pressure sensor 24 which is connected via a data line 25 to computing and analyzing unit 20.

The dialysis apparatus may also have other components, for example a balancing device and an ultrafiltration device, which however have not been represented for the sake of greater clarity.

The example device for the operation of blood pump 6 is described in the present example embodiment as a component part of the extracorporeal blood treatment apparatus, whereby the monitoring of the proper operation of the blood pump is possible. In principle, however, the proper operation of other involved pumps, for example the substitute pump, may also be monitored.

Even though the device for the operation of an electric peristaltic hose pump is described in the present example of embodiment in connection with an extracorporeal blood treatment apparatus, the device for the operation of the hose pump can however also form an independent subassembly, which may be used in any medical-technical apparatuses where the monitoring of the proper operation of hose pumps is desired.

The mode of operation of the device for the operation of blood pump 6 is explained in detail below.

Figure 3A:
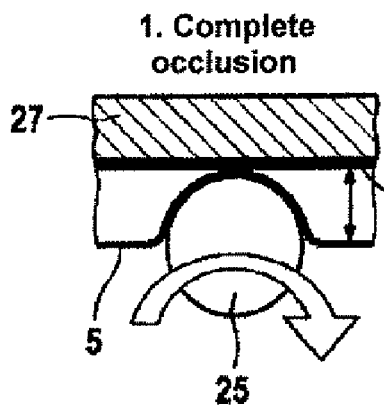
FIGS. 3a to 3c show the dynamic pressure characteristics during the operation of a roller pump with complete occlusion, at the start of a vanishing occlusion and with an incomplete occlusion of the hose line.
Figure 3A:
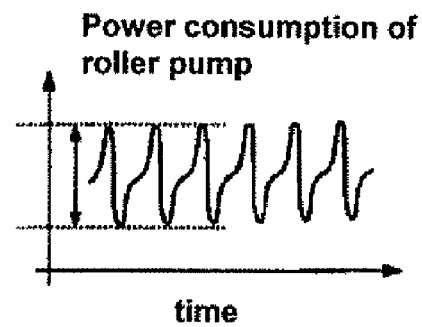
Figure 3B:
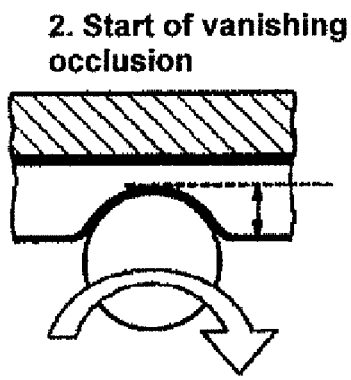
Figure 3B:
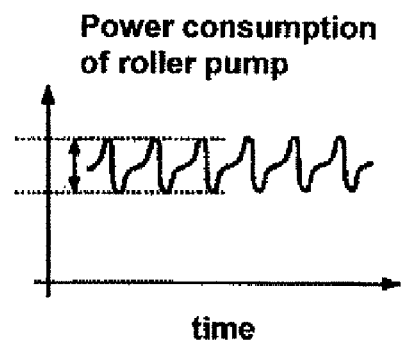
Figure 3C:
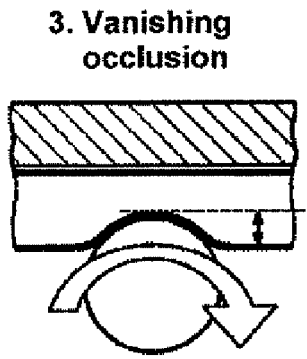
Figure 3C:
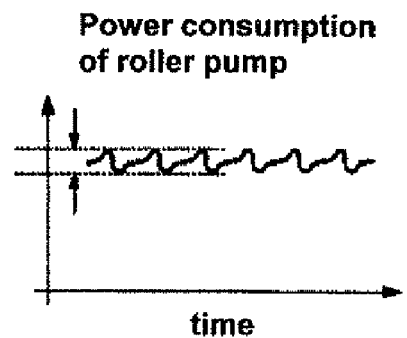

Blood pump 6 is a roller pump. Since roller pumps are generally known, a detailed description is not required. FIGS. 3a to 3c show a schematic diagram of the mode of operation of the roller pump, whereby only one of rollers 25 is shown. Rollers 25 are mounted rotatably on a rotor not shown. The hose line, in the present example arterial blood line 5, is located between rollers 25 and a stator 27, which forms a roller path 28 as a counter-bearing.

FIGS. 3a to 3c show only a schematic diagram. In the case of roller pumps, the roller path extends in an arc-shape around the rotor fitted with rollers. Rollers 25 are pretensioned in a spring-mounted manner on the rotor against roller path 28, so that the rollers can rise from the hose line.

FIG. 3a shows the case where rollers 25 completely occlude the hose line, FIG. 3b the case where the rollers are beginning to rise from the hose line and FIG. 3c the case where the hose line is no longer completely occluded by the rollers, so that the blood pump no longer operates correctly.

The monitoring of the operation of the blood pump is based on the evaluation of the power consumed by the pump. The power consumption may be calculated from the product of the voltage present at the direct current motor of blood pump 6 and the current flowing into the motor. It also suffices, however, to determine a magnitude correlating with the power. Since the voltage may be assumed as constant, it is sufficient to measure the motor current alone. It should be pointed out that the blood pump can in principle also be operated with an alternating current motor.

The flow resistance in the dialyzer can rise during an extra-corporeal blood treatment (clotting). This leads to an increase in the pressure in arterial blood line 5 upstream of blood pump 6 and downstream of dialyzer 1, but this cannot be measured with venous pressure sensor 24. The power consumption of blood pump 6 increases with increasing arterial pressure.

An analysis of the power consumption shows that the power consumed by the pump or a physical magnitude correlating with the power has both a direct component that does not change periodically and an alternating component that does change periodically.

Figure 2:
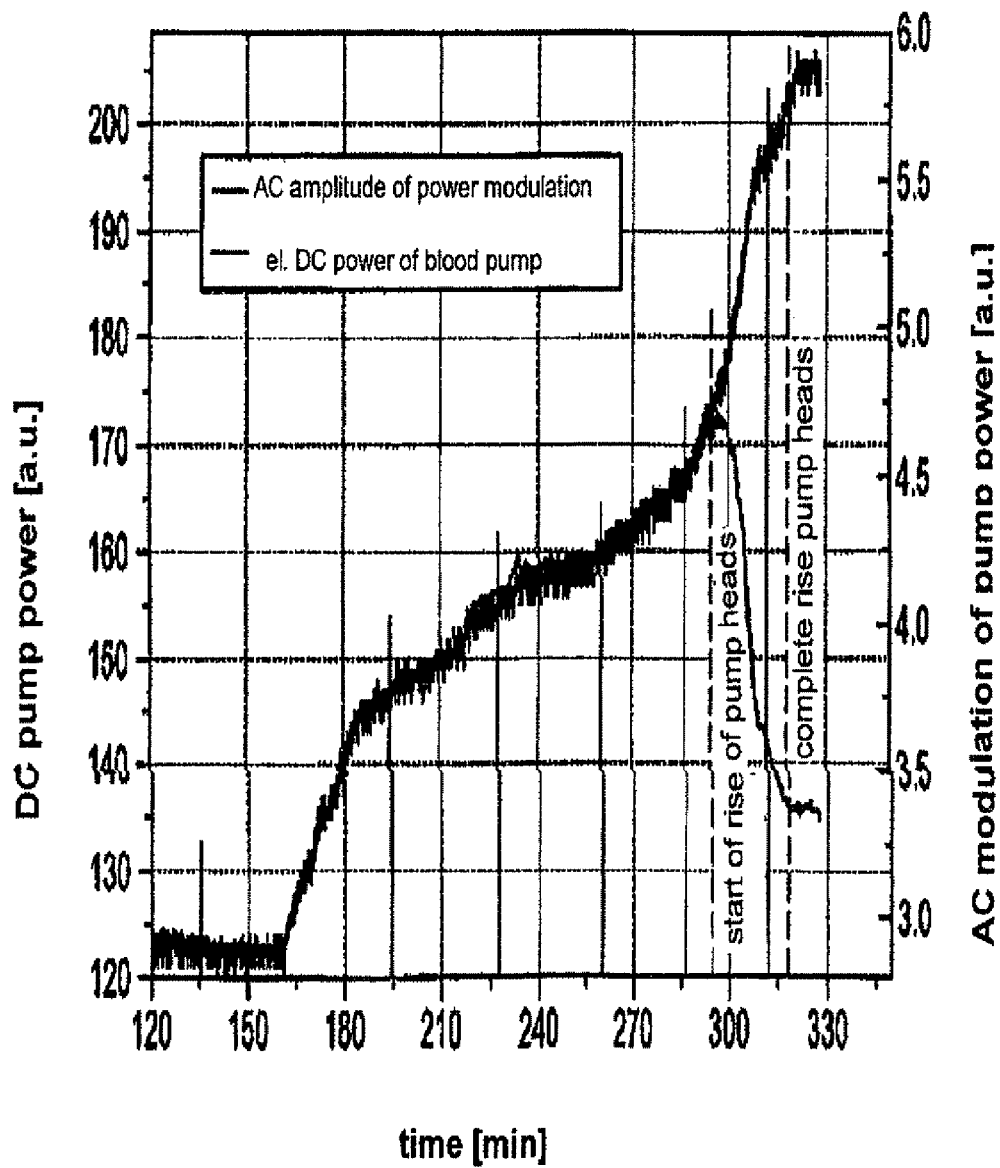
FIG. 2 shows the direct and alternating component of the power consumption of the blood pump during a dialysis treatment as a function of the treatment period.

FIG. 2 shows the power consumption of the blood pump as a function of time with regard to the direct component (DC) and the alternating component (AC).

The magnitude of the AC power consumption runs proportional to the magnitude of the DC power consumption if the blood pump occludes completely. By suitable scaling, the curves can be made to coincide in this case. If, however, the rollers of the blood pump rise from the blood hose segment, so that the delivery rate of the pump diminishes, the coincidence disappears. This is shown graphically in FIG. 2 during an in-vitro dialysis treatment with blood substitute. During this treatment, the blood substitute was thickened to the extent of clotting the dialyzer due to excessive ultrafiltration, so that the flow resistance in the dialyzer constantly increased, until the resistance force exceeded the restoring forces of the rollers of the pump on account of the raised dynamic pressure and the occlusion began to disappear. Due to the reduction of the stroke of the pump rollers, the modulation width of the consumed power of the motor diminishes, although the average power consumption increases on account of the high flow resistance in the hose segment.

FIGS. 3a to 3c show that the amplitude of the AC power consumption diminishes with the disappearance of the occlusion, whereas the PC power consumption increases with the disappearance of the occlusion.

The blood treatment apparatus according to the invention operates as follows:

To prepare the dialysis treatment, control unit 16 sets a value for blood flow rate $Q_b$ which is so small that the flow resistance through the dialyzer is negligible. The pressure in arterial blood line 5 upstream of dialyzer 1 then corresponds to the pressure that venous pressure sensor 24 measures. The current of pump 6 is now measured. Measured pump current $I_{p1}$ corresponds to pressure $P_{ven}$.

$$I(p=P_{ven}(Q_b\approx0))I_{p1} \quad \text{(Equation 1)}$$

Control unit 16 then closes venous shut-off valve 12 and other valves (not shown for the sake of greater clarity) in dialyzing fluid supply line and discharge line 13, 14, so that blood pump 6 now works against the pressure which the restoring forces of the rollers are in a position to produce. In the case of roller pumps used in practice, this pressure lies technically and according to standard at approx. 1.6 to 1.8 bar. The current consumption of the blood pump thus corresponds to a pressure of 1.6 to 1.8 bar.

$$I(p=P_{occ})=I_{p2} \quad \text{(Equation 2)}$$

The pressure may be determined from current consumption I according to the linear relationship between the power consumption and pressure p(I) upstream of the dialyzer:

$$I_p(p) = \quad \text{(Equation 3)}$$
$$\frac{I_{p2} - I_{p1}}{P_{Okk} - P_{ven}(Q_b = 0)}(p - P_{ven}(Q_b = 0)) + I_{p1} \Rightarrow p(I) =$$
$$\frac{P_{Okk} - P_{ven}(Q_b = 0)}{I_{p2} - I_{p1}}(I - I_{p1}) + P_{ven}(Q_b = 0)$$

The magnitudes given in equation 3 are available to computing and analyzing unit 20. Venous pressure $P_{ven}$ is measured with venous pressure sensor 24 while blood pump 6 is operated at minimum delivery rate, whereby current $I_{p1}$ is measured or preset by control unit 16. The pressure in arterial blood line 6 $P_{occ}$, which is dependent on the type of pump, is assumed at a value lying between 1.6 and 1.8 bar.

During the blood treatment, the arterial pressure in arterial blood line 5 is calculated continuously by computing and analyzing unit 20 according to equation 3.

During the blood treatment, moreover, computing and analyzing unit 20 continuously determines the direct component (DC power consumption) and alternating component (AC power consumption) from the power consumption or a physical magnitude correlating with the power consumption, in particular from the pump current. The frequency resulting from the product of the rotor frequency and the number of rollers forms the basis for the alternating component. As long as the blood pump completely occludes the hose line, the quotient of the time-related change in the amplitude of the AC power consumption $A_{AC}$ and the time-related change in the DC power consumption $I_{DC}$ is constant, i.e. the gradients of amplitude modulation $A_{AC}$ and the value of mean direct current consumption $I_{DC}$ run in a linear relationship with one another.

$$\frac{\frac{d}{dt}A_{AC}}{\frac{d}{dt}I_{DC}} = \frac{dA_{AC}}{dI_{DC}} = const, \quad \text{(Equation 4)}$$

where, with T as the periodicity of the blood pump standardized to the number of rollers and φ as the standardization of the phase position, i.e. the phase shift between modulation $A_{AC}$ and trigonometric function sin(x) used in the integration interval, the following holds:

$$I_{DC} = \frac{1}{T}\int_T I(t)dt \quad \text{(Equation 5)}$$

$$A_{AC} = \frac{1}{T}\int_T I(t)\sin\left(2\pi\frac{t}{T}+\varphi\right)dt \quad \text{(Equation 6)}$$

If the ratio given in equation 4 is no longer constant, but begins to tend towards zero, the occlusion of the blood pump diminishes, i.e. the rollers of the blood pump rise from the hose segment. This is particularly the case when the ratio assumes a negative sign.

$$\frac{\frac{d}{dt}A_{AC}}{\frac{d}{dt}I_{DC}} = \frac{dA_{AC}}{dI_{DC}} \leq 0 \quad \text{(Equation 7)}$$

With complete elimination of occlusion, the following then holds:

$$\frac{d}{dt}I_{DC} = 0, \quad \text{(Equation 8)}$$

$$\frac{d}{dt}A_{AC} = 0 \quad \text{(Equation 9)}$$

During the treatment, computing and analyzing unit 20 continuously calculates the quotient of the time-related change in AC power consumption $A_{AC}$ and DC power consumption $I_{DC}$ according to equation 4. Computing and analyzing unit 20 has a microprocessor for performing the necessary computing operations, in particular for forming the differentials.

Computing and analyzing unit 20 compares the ascertained quotient with preset limiting values. In the event that the ascertained quotient is greater than a first preset limiting value, i.e. is constant (equation 4), it is assumed that blood pump 6 is completely occluding arterial blood line 5 (FIG. 3*a*). If, however, the first limiting value is fallen below, computing and analyzing unit 20 generates a first alarm signal, so that alarm unit 23 emits a first optical and/or acoustic alarm, which signals that the rollers of the blood pump are beginning to rise from the hose line (FIG. 3*b*). If a further second limiting value, which is smaller than the first limiting value, is fallen below, the computing and analyzing unit generates a second alarm signal, so that the alarm device emits a second alarm, which signals that the blood pump is no longer completely occluding the hose line (FIG. 3*c*). A proper operation of the hose pump is then no longer present, since the pressure in arterial blood line 5 has exceeded a preset limiting value on account of an increase in the flow resistance in dialyzer 1.

An alternative embodiment makes provision not to compare the quotient with a limiting value, but to link together logically in the following manner the time-related change in the direct component and alternating component of the power consumption in preset time intervals, i.e., the measure of the increase (gradient) of the magnitudes.

If both the direct component and the alternating component of the power consumption rise, the conclusion is drawn that the arterial pressure is increasing. If only the direct component of the power consumption rises, but the alternating component of the power consumption remains at a standstill, the conclusion is drawn that the occlusion of the blood pump is beginning to diminish. If the alternating component of the power consumption begins to fall with an increasing direct component of the power consumption, the conclusion is drawn that the rollers of the blood pump have risen from the hose line. In the event that, after the rising of the pump rollers, both the direct component and the alternating component of the power consumption remain at a standstill, computing and analysing unit 20 ascertains that blood pump 6 is no longer delivering.

In principle, it is also possible to link the two evaluation procedures to one another, whereby both the fact that preset limiting values are exceeded or fallen below and also a logic AND linking of the direct and alternating component of the power consumption are taken into account.

It is also possible solely to monitor the quotient of the direct component and alternating component. As can be seen from FIG. 2, this quotient remains constant in a certain range, as long as the pump is operating in a non-occluding manner. The deviation of the curve shape at a later time, however, leads to a change (reduction) in the quotient which is detected as a malfunction.

The invention claimed is:

1. A method for the operation of an electric peristaltic hose pump for conveying a fluid in a hose line, comprising:
   determining the power consumed by the pump or determining a physical magnitude correlating with the power consumed by the pump;
   determining, based on the determined power or the determined physical magnitude, a direct component that does not change periodically and an alternating component that changes periodically and is superimposed on the direct component; and
   concluding that there is an incorrect operation of the hose pump on the basis of the direct component and the alternating component during the operation of the hose pump.

2. The method according to claim 1, wherein the concluding step includes ascertaining a relationship between a time-related change in the direct component (d/dt IDC) and a time-related change in the alternating component (d/dt AAC) in preset time intervals, whereby it is concluded that there is an incorrect operation of the hose pump on the basis of the time-related change in the ascertained relationship between the time-related change in the direct component and alternating component in preset time intervals during the operation of the hose pump.

3. The method according to claim 2, wherein the concluding step further includes calculating in present time intervals a quotient (dAAC/dIDC) of the time-related change in the alternating component (d/dt AAC) and the direct component (d/dtIDC), and comparing the quotient with a preset limiting value, whereby it is concluded that there is an inadequate occlusion of the hose pump if the quotient falls below the preset limiting value.

4. The method according to claim 1, wherein the concluding step includes calculating in present time intervals a quotient (AAC/IDC) of the alternating component (AAC) and the direct component (IDC), and comparing the quotient with a preset limiting value, whereby it is concluded that there is an inadequate occlusion of the hose pump if the quotient falls below the preset limiting value.

5. The method according to claim 1, wherein the hose pump is an occlusive roller pump, wherein the hose line is inserted between a stator, which forms a roller path as a counter-bearing, and a rotor, which is fitted with rollers mounted rotatably.

6. The method according to claim 1, further comprising determining a pressure downstream of the hose pump from the power or the physical magnitude correlating with the power.

7. The method according to claim 1, wherein the electric peristaltic hose pump for conveying a fluid in a hose line is an electric peristaltic hose pump of an extracorporeal blood treatment apparatus.

8. The method according to claim 7, wherein the peristaltic hose pump is arranged in an arterial hose line, which leads to a blood treatment unit, from which a venous hose line departs, wherein the arterial and venous hose line together with the blood treatment unit form an extracorporeal blood circuit.

9. A device for the operation of an electric peristaltic hose pump for conveying a fluid in a hose line, comprising:
   an arrangement configured to determine the power consumed by the pump during the operation of the pump or a physical magnitude correlating with the power consumed during the operation of the pump, the arrangement including
      a first component configured to determine from the determined power consumed by the pump or the determined physical magnitude, a direct component which does not change periodically and an alternating component which does change periodically, and
      a second component configured to determine an incorrect operation of the hose pump, the second component being arranged in such a way that it is concluded that there is an incorrect operation of the hose pump on the basis of the direct component and the alternating component during the operation of the hose pump.

10. The device according to claim 9, wherein the second component is designed in such a way that a time-related change in the direct component (d/dt IDC) and a time-related change in the alternating component (d/dt AAC) in preset time intervals during the operation of the hose pump are put into a relationship with one another, whereby it is concluded that there is an incorrect operation of the hose pump on the basis of the time-related change in the ascertained relationship between the time-related change in the direct component and alternating component in preset time intervals during the operation of the hose pump.

11. The device according to claim 10, wherein the second component is designed in such a way that a quotient (dAAC/dIDC) of the time-related change in the alternating component (d/dt AAC) and the direct component (d/dt IDC) is calculated in preset time intervals during the operation of the hose pump and compared with a preset limiting value, whereby it is concluded that there is an inadequate occlusion of the hose pump if the quotient falls below the preset limiting value.

12. The device according to claim 9, wherein the second component is designed in such a way that a quotient (AAC/IDC) of the alternating component (AAC) and the direct component (IDC) is calculated in preset time intervals during the operation of the hose pump and compared with a preset limiting value, whereby it is concluded that there is an inadequate occlusion of the hose pump if the quotient falls below the preset limiting value.

13. The device according to claim 9, wherein the hose pump is an occlusive roller pump, and wherein the hose line is arranged between a stator, which forms a roller path as a counter-bearing, and a rotor, which is fitted with rollers mounted in a rotatably.

14. The device according to claim 9, further comprising an arrangement for determining the pressure downstream of the hose pump, the arrangement designed in such a way that the pressure downstream of the hose pump is determined from the determined power or the determined physical magnitude correlating with the power.

15. A blood treatment apparatus comprising:
   an electric peristaltic hose pump; and
   a device according to claim 9 for the operation of the peristaltic hose pump.

16. The blood treatment apparatus according to claim 15, wherein the blood treatment apparatus further comprises a blood treatment unit, to which an arterial hose line leads and from which a venous hose line departs, wherein the electric peristaltic hose pump is arranged in the arterial hose line.

* * * * *